United States Patent
Tokuchi et al.

(10) Patent No.: US 10,646,163 B2
(45) Date of Patent: May 12, 2020

(54) INFORMATION PROCESSING SYSTEM

(71) Applicant: FUJI XEROX CO., LTD., Tokyo (JP)

(72) Inventors: Kengo Tokuchi, Kanagawa (JP); Yukari Sai, Tokyo (JP); Mizuha Marumoto, Tokyo (JP); Yuka Nomura, Kanagawa (JP); Yukiko Miyakoshi, Kanagawa (JP)

(73) Assignee: FUJI XEROX CO., LTD., Tokyo (JP)

( * ) Notice: Subject to any disclaimer, the term of this patent is extended or adjusted under 35 U.S.C. 154(b) by 0 days.

(21) Appl. No.: 16/120,736

(22) Filed: Sep. 4, 2018

(65) Prior Publication Data
US 2019/0239814 A1     Aug. 8, 2019

(30) Foreign Application Priority Data

Feb. 2, 2018 (JP) .................... 2018-017269

(51) Int. Cl.
*A61B 5/00* (2006.01)
*G08B 5/22* (2006.01)
*A61B 5/11* (2006.01)
*A47C 31/11* (2006.01)
*A47G 9/02* (2006.01)

(52) U.S. Cl.
CPC ............ *A61B 5/6892* (2013.01); *A47C 31/11* (2013.01); *A47G 9/0223* (2013.01); *A61B 5/1116* (2013.01); *G08B 5/22* (2013.01); *A61B 2560/0252* (2013.01); *A61B 2562/029* (2013.01)

(58) Field of Classification Search
CPC ...... A61B 2560/0252; A61B 2562/029; A61B 5/1116; G08B 5/22
See application file for complete search history.

(56) References Cited

U.S. PATENT DOCUMENTS

| | | | |
|---|---|---|---|
| 2003/0025601 A1 * | 2/2003 | Gruteser | A47C 15/004 340/540 |
| 2012/0283929 A1 * | 11/2012 | Wakita | A61G 5/04 701/99 |
| 2015/0382150 A1 * | 12/2015 | Ansermet | H04B 5/0031 455/41.1 |
| 2017/0215736 A1 | 8/2017 | Hu | |
| 2019/0003877 A1 * | 1/2019 | Aina | B60N 2/002 |

FOREIGN PATENT DOCUMENTS

JP         2017-23475 A       2/2017

\* cited by examiner

*Primary Examiner* — Omeed Alizada
(74) *Attorney, Agent, or Firm* — Oliff PLC

(57) ABSTRACT

An information processing system includes a sheet-shaped apparatus placed in a specific place, the sheet-shaped apparatus including a sensor built in the sheet-shaped apparatus to sense information indicating whether a user is present over the place in which the sheet-shaped apparatus is placed, an acquiring unit that acquires environmental information about the place, and a providing unit that provides information based on the information sensed by the sensor and on the environmental information acquired by the acquiring unit.

7 Claims, 5 Drawing Sheets

FIG. 5

| SEAT ID | TEMPERATURE SENSOR | HUMIDITY SENSOR | ILLUMINANCE SENSOR | NOISE SENSOR |
|---|---|---|---|---|
| 01 | TS01 | MS01 | LS01 | NS01 |
| 02 | TS01 | MS01 | LS02 | NS01 |
| 03 | TS01 | MS01 | LS03 | NS02 |
| 04 | TS02 | MS02 | LS04 | NS02 |
| ⋮ | ⋮ | ⋮ | ⋮ | ⋮ |

FIG. 6

| SEAT ID | STATUS | TEMPERATURE | HUMIDITY | BRIGHTNESS | NOISE |
|---|---|---|---|---|---|
| 01 | SEATED | 22.3 | 55 | 5 | 40 |
| 02 | SEATED | 22.4 | 55 | 5 | 48 |
| 03 | UNSEATED | 22.2 | 55 | 4 | 60 |
| 04 | SEATED | 22.2 | 55 | 4 | 56 |
| ⋮ | ⋮ | ⋮ | ⋮ | ⋮ | ⋮ |

FIG. 7

| SEAT 01 | | | | | |
|---|---|---|---|---|---|
| DATE/TIME | STATUS | TEMPERATURE | HUMIDITY | BRIGHTNESS | NOISE |
| 22/1 9:00 | UNSEATED | 21.0 | 54 | 4 | 38 |
| 22/1 9:05 | SEATED | 21.2 | 54 | 5 | 40 |
| 22/1 9:10 | SEATED | 22.0 | 55 | 5 | 40 |
| 22/1 9:15 | SEATED | 22.0 | 55 | 5 | 42 |
| ⋮ | ⋮ | ⋮ | ⋮ | ⋮ | ⋮ |

FIG. 8

| SEAT ID | STATUS | TEMPERATURE | HUMIDITY |
|---|---|---|---|
| 01 | OCCUPIED | 22.5 | 55 |
| 02 | VACANT | 22.1 | 54 |
| 03 | OCCUPIED | 22.4 | 55 |
| 04 | BEING CLEANED | 22.5 | 55 |
| ⋮ | ⋮ | ⋮ | ⋮ |

INFORMATION PROCESSING SYSTEM

CROSS-REFERENCE TO RELATED APPLICATIONS

This application is based on and claims priority under 35 U.S.C. 119 from Japanese Patent Application No. 2018-017269 filed Feb. 2, 2018.

BACKGROUND

Technical Field

The present invention relates to an information processing system.

SUMMARY

According to an aspect of the invention, there is provided an information processing system including a sheet-shaped apparatus placed in a specific place, the sheet-shaped apparatus including a sensor built in the sheet-shaped apparatus to sense information indicating whether a user is present over the place in which the sheet-shaped apparatus is placed, an acquiring unit that acquires environmental information about the place, and a providing unit that provides information based on the information sensed by the sensor and on the environmental information acquired by the acquiring unit.

BRIEF DESCRIPTION OF THE DRAWINGS

Exemplary embodiment of the present invention will be described in detail based on the following figures, wherein:

FIG. 5 illustrates exemplary management information for managing the correspondence between a seat and a group of sensors used to sense environmental information about the seat such as temperature;

FIG. 6 illustrates exemplary information indicative of the current seating status of each seat, and environmental information such as temperature;

FIG. 7 illustrates an example of the seating status of a seat and environmental information about the seat for various times in the past stored in a database;

FIG. 8 illustrates exemplary management information for managing the status of each seat within an establishment;

DETAILED DESCRIPTION

An example of a sheet-shaped apparatus 100 according to an exemplary embodiment will be described below with reference to FIGS. 1 and 2.

Figure 1:
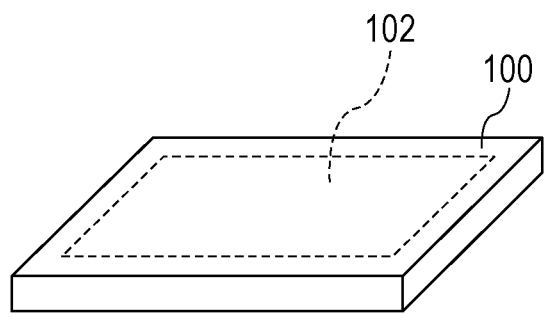
FIG. 1 schematically illustrates the outward appearance of a sheet-shaped apparatus (in the form of a cushion)

In the example illustrated in FIG. 1, the sheet-shaped apparatus 100 is implemented as, for example, a cushion placed on a seat such as a chair. Although the sheet-shaped apparatus 100 has a rectangular top face in FIG. 1, this is intended to be illustrative only. The sheet-shaped apparatus 100 may have a top face in another shape.

Figure 2:
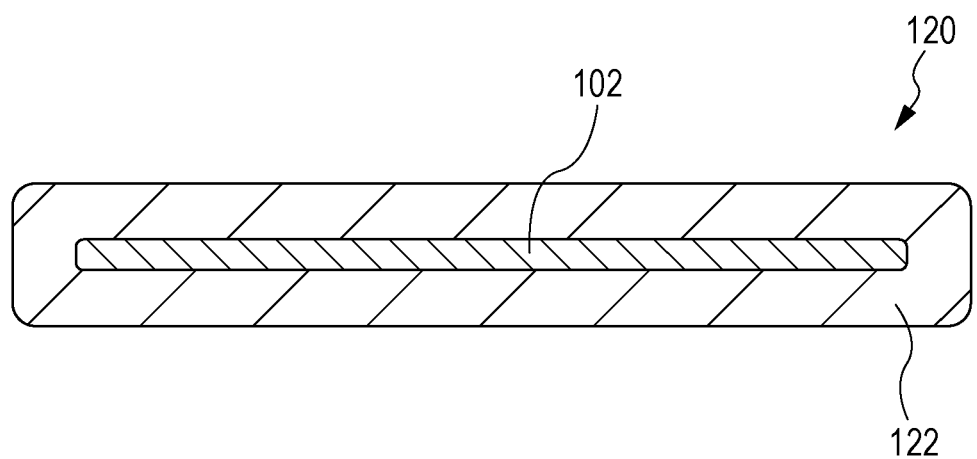
FIG. 2 schematically illustrates the cross-sectional structure of a sheet-shaped apparatus.

FIG. 2 illustrates a body portion 120 of the sheet-shaped apparatus 100. The body portion 120 includes a base 122, and a sheet-shaped pressure distribution sensor 102 attached to the interior or surface of the base 122. The pressure distribution sensor 102, which is a sensor used to measure in-plane pressure distribution, has a generally flexible structure. The pressure distribution sensor 102 senses the distribution of pressure exerted from the body of the user sitting on the sheet-shaped apparatus 100. The pressure distribution sensor 102 is able to determine whether a person is sitting on the sheet-shaped apparatus 100 (and therefore, the seat) by determining whether a value obtained by integrating the pressure detected by the pressure distribution sensor 102 with respect to area corresponds to a human person's weight. It is also possible to use this pressure distribution to, for example, determine whether the user's sitting posture is good.

In addition to the above-mentioned components, the following components are built in the body portion 120: a controller 110 (see FIG. 3) including components such as a processor, a random access memory (RAM), a read-only memory (ROM), and a writable non-volatile storage medium; a power supply circuit, a built-in battery, or other power supplies used to supply electricity to the controller 110 and to other pieces of electrical equipment; and wires between the above-mentioned pieces of electrical equipment. Sensors other than the pressure distribution sensor 102 may be attached to the body portion 120. Examples of sensors attached to the body portion 120 include a temperature sensor, a humidity sensor, a location sensor that employs a GPS or other positioning systems, and a sensor according to related art that employs an optical fiber array arranged in a sheet-shaped configuration (to be referred to as "sensor sheet" hereinafter).

The sheet-shaped apparatus 100 is formed by covering the body portion 120 with a covering (not illustrated). The covering may be made from, for example, a piece of fabric made by weaving or knitting of natural fibers, such as wool, chemical fibers, or other fibers. The covering may be removable from the body portion 120 so that when, for example, the covering becomes soiled or dirty, the covering may be detached from the body portion 120 for washing.

Figure 3:
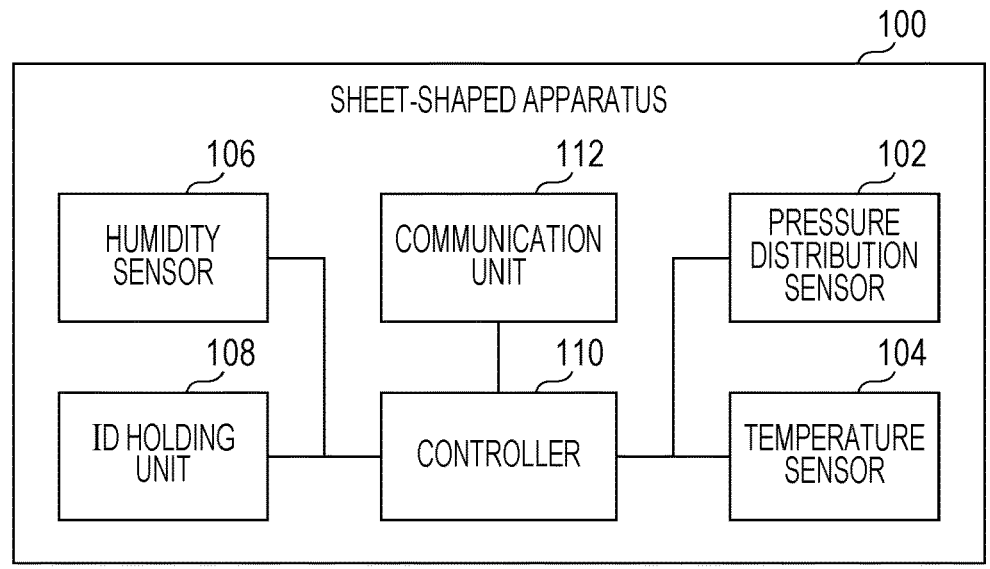
FIG. 3 illustrates the functional configuration of a sheet-shaped apparatus.

Next, an exemplary electrical functional configuration of the sheet-shaped apparatus 100 will be described with reference to FIG. 3. In the example illustrated in FIG. 3, the sheet-shaped apparatus 100 includes the pressure distribution sensor 102, a temperature sensor 104, a sensor sheet 106, an ID holding unit 108, the controller 110, and a communication unit 112. The pressure distribution sensor 102 has already been described above.

The temperature sensor 104 senses the temperature of the sheet-shaped apparatus 100. For instance, when the user is sitting on the sheet-shaped apparatus 100 placed on a seat, the temperature sensor 104 senses a temperature close to the body temperature of the user. The sensor sheet 106 includes an optical fiber array sheet according to related art, a light source, a photodetector, a signal processing circuit, and a control circuit. The control circuit controls the light source or other components to perform a control such that a predetermined input light signal is supplied to the optical fiber array sheet. The signal processing circuit converts an output light signal from the optical fiber array sheet into an electrical signal, and performs an analysis according to related art to extract the user's pulse and other information of interest.

The ID holding unit 108 holds identification information (ID) that uniquely identifies the sheet-shaped apparatus 100. The ID is used to, for example, indicate the origin of information (e.g., sensing data from each sensor or analysis results on the sensing data) sent from the sheet-shaped apparatus 100 to a management apparatus 200 (see FIG. 4).

Now, a case is considered where, for example, in an environment with multiple seats present, the seat on which to place a given sheet-shaped apparatus 100 is changed (e.g., the user moves to another seat while carrying the sheet-shaped apparatus 100). For such a case, instead of or in addition to the ID of a sheet, the ID of a seat on which the sheet is placed s associated with information transmitted from the sheet-shaped apparatus 100. This may be accomplished by, for example, the sheet-shaped apparatus 100 receiving the ID of the seat from an ID holding unit attached to the seat. The ID holding unit attached to the seat may be implemented as a near field communication (NFC) tag. In this case, an NFC reader included in the sheet-shaped apparatus 100 reads the ID held by the tag.

The controller 110 receives sensing data from each sensor such as the pressure distribution sensor 102, and processes each such piece of sensing data. Examples of processes executed by the controller 110 may include a process that transmits a group of pieces of such sensing data to the management apparatus 200 or to another apparatus on a network such as a server via the communication unit 112. The controller 110 may analyze sensing data acquired from the group of sensors to obtain analysis results. An example of this analysis involves determining, from a pressure distribution sensed by the pressure distribution sensor 102, whether the user's sitting posture is good or the type of the sitting posture. If the sheet-shaped apparatus 100 has a built-in device that exerts an external effect, such as a heater, the controller 110 may control operation of the device in accordance with information such as the determined sitting posture and the results of analysis of sensing data obtained from the group of sensors.

The communication unit 112 is used to perform data communications that comply with a given communication standard. In one example, the communication unit 112 communicates with the management apparatus 200 in compliance with a wireless communication standard such as a wireless LAN or Bluetooth (registered trademark). In the present example, the communication unit 112 sends, under control by the controller 110, sensing data obtained from the group of sensors mentioned above, the results of analysis of the sensing data, or other information to the management apparatus 200.

Figure 4:
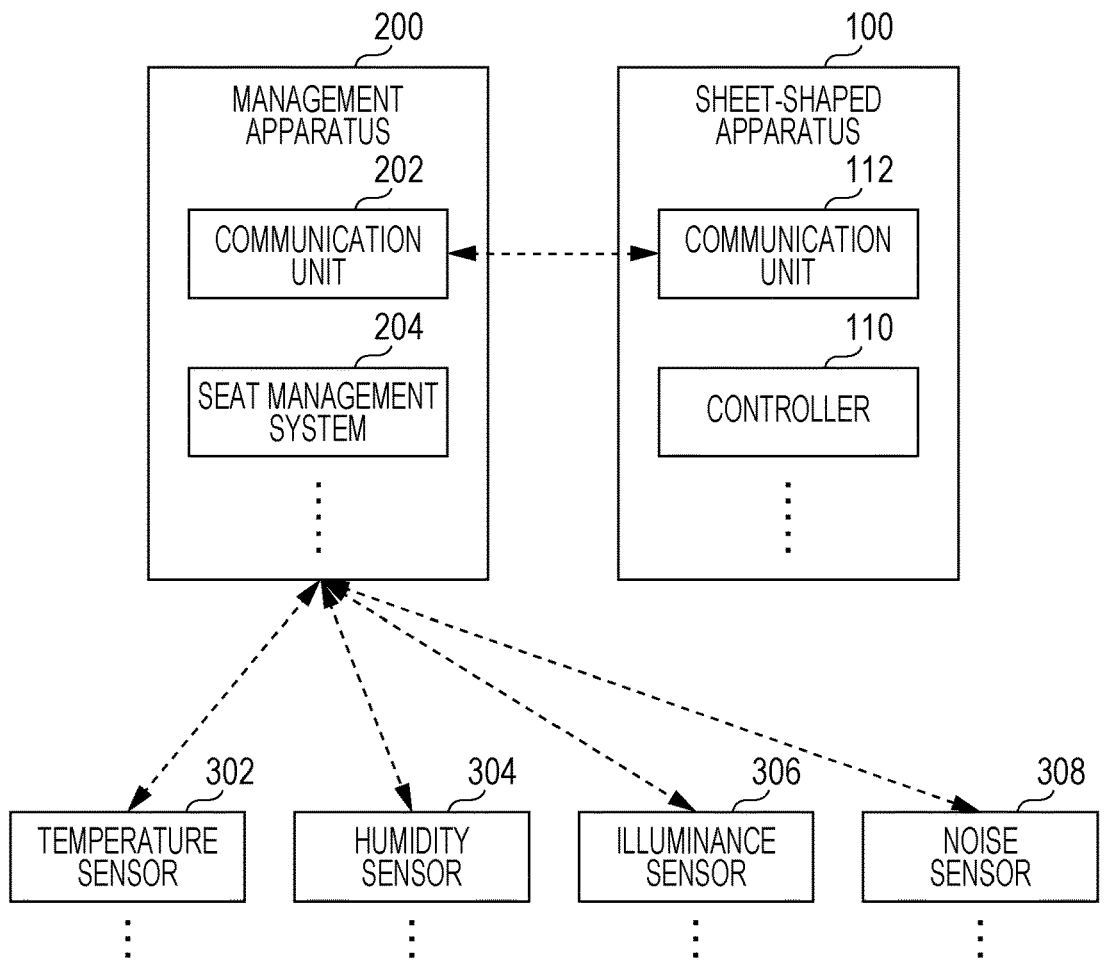
FIG. 4 illustrates the functional configuration of a system including a sheet-shaped apparatus and a management apparatus.

Next, an exemplary system configuration according to the exemplary embodiment will be described with reference to FIG. 4. Although not illustrated, this system is used for facilities with multiple seats present, such as offices or eating establishments. Typically, the sheet-shaped apparatus 100 is placed for each of such multiple seats.

The management apparatus 200 performs recording or analysis of information sent from the sheet-shaped apparatus 100 located at each seat, presentation of the information to the manager, or other operations. The management apparatus 200 is an apparatus with a built-in computer, examples of which include a personal computer (PC), a tablet terminal, and a smart phone. The management apparatus 200 includes a communication unit 202. In the example illustrated in FIG. 4, the communication unit 202 enables wireless communication with the communication unit 112 of the sheet-shaped apparatus 100.

Various sensors are disposed in various places within a facility to sense the environment condition in each place. Such sensors include, for example, a temperature sensor 302, a humidity sensor 304, an illuminance sensor 306, and a noise sensor 308. Although it may not be necessary to provide such sensors for each seat, to enable sensing of the environment of each individual seat with maximum possible precision, these sensors are provided for each area where several seats are present. Such a group of sensors is provided for, for example, structural objects of the facility, such as the wall, the ceiling, and the floor, or for objects placed within the facility, such as a counter, a shelf, and a table. As these sensors, sensors provided for equipment disposed within the facility for other purposes may be also used. For example, a temperature sensor or humidity sensor provided to each of several air-conditioners disposed within the facility or to the operation panel of the air-conditioner may be employed as the temperature sensor 302 or the humidity sensor 304 used for several seats located near the air conditioner or other equipment. The illuminance sensor 306, which is used to sense the rough brightness of a seat, does not need to be provided for each seat. For example, the illuminance sensor 306 may be provided to a table with multiple seats placed around the seat. In this case, the brightness sensed by the illuminance sensor provided to the table is regarded as representing the brightness of the multiple seats. The types of sensors depicted in FIG. 4, such as the temperature sensor 302, the humidity sensor 304, the illuminance sensor 306, and the noise sensor 308, are for illustrative purposes only. Types of sensors other than those mentioned above may be placed. Further, not all of the illustrated types of sensors need to be placed.

Each of the temperature sensor 302, the humidity sensor 304, the illuminance sensor 306, and the noise sensor 308 transmits, at regular time intervals, for example, information (sensing data) sensed by the sensor to the management apparatus 200 in association with a sensor ID representing the ID of the sensor.

The management apparatus 200 is installed with a seat management system 204. The seat management system 204 is a system that manages pieces of information received from components such as the sheet-shaped apparatus 100 located at each seat, and a group of sensors such as the temperature sensor 302, the humidity sensor 304, the illuminance sensor 306, and the noise sensor 308. The seat management system 204 performs operations such as recording the pieces of received information, or providing the facility's user or the facility's manager with information obtained by analyzing the pieces of received information or by analyzing recorded past information.

The seat management system 204 performs operations such as recording information received from the sheet-shaped apparatus 100 located at each seat, in association with sensing data received from each of the temperature sensor 302, the humidity sensor 304, the illuminance sensor 306, and the noise sensor 308 that are located near the seat, or analyzing the received information in combination with each piece of such sensing data. To this end, as illustrated in FIG. 5, the seat management system 204 holds a table representing the correspondence between the ID of a seat, and the IDs of various nearby sensors associated with the seat. This table is set by, for example, a manager who manages the management apparatus 200.

The following describes one implementation of the exemplary embodiment as applied to the management or analysis of seat usage status in free address offices.

In free address offices, employees are not assigned fixed seats. Instead, there are a large number of seats that are available for anyone to use. When performing a task in such an office, an employee finds a desired seat from among vacant seats, and sits in the seat to perform the task. In this case, it is possible that some seats are more popular than others. An ability to determine the cause of such a difference in the relative popularity of seats would lead to improved office layout. Accordingly, in the present example, an analysis is performed by using information sensed by the sheet-shaped apparatuses 100 placed on individual seats, and information sensed by sensors that measure the ambient environment of each of those seats.

The controller 110 of the sheet-shaped apparatus 100 transmits, to the management apparatus 200 at regular time intervals, for example, sensing data (i.e., information about a pressure distribution) obtained from the pressure distribution sensor 102, or information indicating whether the user is seated on the sheet-shaped apparatus 100, which can be determined from the pressure distribution. In an alternative configuration, when the controller 110 senses, from sensing data obtained from the pressure distribution sensor 102, a change in seating status from unseated to seated or the opposite change in seating status, the controller 110 may notify the management apparatus 200 of the sensed change.

Likewise, the temperature sensor 302, the humidity sensor 304, the illuminance sensor 306, and the noise sensor 308, which are placed in various places within the facility, also transmit their sensing information to the management apparatus 200 at regular time intervals, for example.

The seat management system 204 of the management apparatus 200 may manage, for example, the following pieces of information for each seat in association with each other as illustrated in FIG. 6: the current seated/unseated status of the seat; and environmental information about the environment of the seat, such as temperature, humidity, brightness, and noise. The current-state information illustrated in FIG. 6 holds, in association with the seat ID of each seat, the status (seated or unseated) of the seat, and environmental information values such as temperature. The seat management system 204 receives the following pieces of information sent from the sheet-shaped apparatus 100: the sheet ID of the sheet-shaped apparatus 100 itself or the seat ID of the seat on which the sheet-shaped apparatus 100 is placed; and sensing data obtained by the pressure distribution sensor 102 or analysis results on the sensing data (the result of seated/unseated status determination). If a sheet ID is sent to the seat management system 204, the seat management system 204 identifies the seat ID corresponding to the sheet ID, and manages the result of seated/unseated status determination in association with the seat ID. Environmental information corresponding to each seat, such as temperature and humidity, is acquired from individual sensors corresponding to the seat, which are specified in the table illustrated in FIG. 5.

The seat management system 204 records, at regular time intervals, for example, the status of a seat, and environmental information about the environment of the seat, such as temperature, into a database (not illustrated) managed by the seat management system 204, in association with the corresponding date and time. FIG. 7 illustrates exemplary information recorded in the database. In the database, the following pieces of information are recorded for each seat ID: the seated/unseated status of the corresponding seat for each date and time, and environmental information about the environment of the seat, such as temperature, humidity, brightness, and noise.

At regular intervals of, for example, every one month, or upon receiving an instruction to execute analysis from the user (who in this case is the manager of the system according to the exemplary embodiment), the seat management system 204 aggregates, for each seat, data stored in the database. This data aggregation involves, for example, calculating the following pieces of information for each seat: the sum of seated times in a specified analysis period (e.g., the period of time from the last execution to the present time if the data aggregation is to be executed regularly); and statistics on various pieces of environmental information for the period, such as temperature, humidity, brightness, and noise level. One example of such statistics is the mean calculated for the period. Other examples of such statistics may include values such as the maximum, minimum, and mode calculated for the period. In addition to the statistics for the entire analysis period, for example, statistics for each set time division may be further calculated, such as the statistics for each time of day (e.g., the sum or mean of seated times, and statistics on environmental information such as temperature, for a time segment from 9 a.m. to 12 a.m.), the statistics for each day of the week, the statistics for weekdays, or the statistics for holidays.

Based on the aggregated results thus obtained for each seat, for example, the seat management system 204 determines a seat to be popular if the seat is higher-ranked in terms of the total seated time, and determines a seat to be unpopular if the seat is lower-ranked in terms of the total seated time. As the criterion for determining whether a seat is popular, for example, either one of the following criteria may be used: whether the total seated time for the seat is greater than or equal to a given threshold; whether the total seated time is within a predetermined rank from the top; and whether the rank of the total seated time is within a predetermined proportion from the top. The criterion for determining whether a seat is unpopular may be defined in a similar manner.

The seat management system 204 displays, on a display attached to the management apparatus 200, an analysis screen for each seat thus determined to be popular or unpopular. The analysis screen displays statistics on environmental information for each such popular or unpopular seat. For example, this screen displays a map of seating layout within a floor of a facility, and shows, on the map, popular seats, unpopular seats, and seats that are neither popular nor unpopular, in mutually distinguishable ways such as by color coding. For each such popular or unpopular seat, the screen also displays a list of statistics on environmental information in the vicinity of where the seat is displayed (or the screen displays, upon selection of a seat on the screen, statistics on the environmental information for the seat). The screen described above is for illustrative purposes only. Similar information may be displayed in other screen layouts. In another example, the seat management system 204 may calculate statistics on environmental information for each of multiple seats determined to be popular and for each of multiple seats determined to be unpopular, and may present a screen that displays the calculated statistics.

The manager uses such an analysis screen to analyze why some seats are popular or unpopular.

Next, the following describes use of the system according to the exemplary embodiment for seating management in eating establishments, such as a cafe.

Seating management is often difficult for eating establishments that are operated in such a way that each customer visiting such an establishment is allowed to find and freely sit in any vacant seat within the establishment. For example, it is often the case that a customer visiting an establishment moves toward a seat thinking that the seat is vacant, only to find that the seat is already being used by another customer (e.g., a case where the visiting customer mistakes a seat for being vacant when in fact another customer using the seat has only left the seat temporarily). After a customer finishes a meal and leaves a seat (table), the seat or table needs to be cleaned for the next customer. However, in situations where, for example, many seats or tables are managed by a small number of staff, it is difficult to clean each such seat or table at the appropriate times or prevent the staff from forgetting to clean each such seat or table.

Accordingly, in the present example, the sheet-shaped apparatus 100 placed on each seat is used to determine whether a customer is seated in the seat, and the result of this determination is used in combination with information from other information sources (which represents a type of environmental information related to the seat) to thereby automatically determine the status of the seat (or the status of a table where the seat is located if it is assumed that customers occupy their seats on a table-by-table basis). Information on the result of this status determination is provided to the staff of the eating establishment to ensure smooth seating management.

The present example assumes that each seat has, for example, the following four statuses: "Vacant", "Occupied", "Being Cleaned", and "Reserved". If multiple seats are placed per table and seat status is managed on a table-by-table basis, the system manages, for each individual table, information indicating which one of the four statuses the table is currently in.

Transitions between the above-mentioned four statuses may be made by using, for example, the following rule.

When the sheet-shaped apparatus 100 placed on a "Vacant" seat senses that a person has sat in the seat (i.e., when sensing data from the pressure distribution sensor 102 changes to one that indicates seating of a person), the status of the seat transitions to "Occupied". For cases where seating is managed on a table-by-table basis, when the sheet-shaped apparatus 100 on one of the seats corresponding to a table in "Vacant" status senses that a person has sat in the seat, the status of the table transitions to "Occupied".

For each seat or table secured upon reservation from a customer, when the seat or table is vacated and reserved, the staff in an establishment sets the status of the seat or table to "Reserved" by operating the management apparatus 200 or a terminal such as a tablet terminal capable of communicating with the management apparatus 200.

For a seat or table in "Reserved" status, when the customer who has reserved the seat or table arrives, the staff in the establishment operates the management apparatus 200 or the terminal to change the status of the seat or table to "Occupied".

For a seat or table in "Occupied" status, its status is changed to "Being Cleaned" upon sensing that the customer has performed an explicit action indicative of the finishing of a meal. If the sheet-shaped apparatus 100 merely senses that the customer has stepped away from the seat, the "Occupied" status is maintained because it is possible that the customer has just left the seat temporarily for reasons such as picking up an item that the customer has ordered self-service or going to the bathroom. An example of an explicit action serving as the condition for causing a status transition from "Occupied" to "Being Cleaned" is the action of taking out, from a predetermined holder, an accounting slip or clipboard clipping the accounting slip, or an accounting tag storing an ID linked to data about customer's orders. This action can be sensed to have been performed when a sensor provided to the holder ceases to sense the presence of an accounting slip, a clipboard, a tag, or other such objects.

For a seat or table in "Being Cleaned" status, after the completion of cleaning, the establishment's staff operates the management apparatus 200 or the terminal capable of communicating with the management apparatus 200 to cause the status of the seat or table to transition to "Vacant".

In this way, the status of a seat or table normally transitions in the following order: "Vacant"→"Occupied"→"Being Cleaned"→"Vacant".

FIG. 8 illustrates exemplary seat status management information managed by the seat management system 204. The illustrated management information holds the following pieces of information in association with the ID of a seat: the status of the seat; and the current environmental information sensed by sensors such as a temperature sensor and a humidity sensor placed near the seat. For cases where seating is managed on a table-by-table basis, the management information to be used holds, in association with the ID of a table instead of the ID of a seat, information such as the status of the table and environmental information about the table. In this case, information representing the correspondence between the ID of a seat or the ID of the sheet-shaped apparatus 100 on the seat, and a table ID is prepared, and this information is used to determine which table the seat seated by a customer corresponds to.

The seat management system 204 causes the status values of each seat within the management information (see FIG. 7) to transition, in accordance with data received from the sheet-shaped apparatus 100 placed on each seat within an establishment, data received from a sensor attached to an accounting slip holder located at a table or seat, or data input to the management apparatus 200 by the establishment's staff. The current status of each seat or table represented by the management information may be displayed in listing form on a display attached to the management apparatus 200 or on a terminal used by the staff, so that each member of the staff is able to check the current state of each seat or table within the establishment. In one non-limiting example, the above-mentioned listing to be displayed may be, for example, a listing of icons displayed on a map of a floor within an establishment to represent each seat or table, with the current status of the seat or table being represented by the manner in which the corresponding icon is displayed (e.g., the color in which the icon is displayed). Each staff member looks at the displayed listing to keep track of the usage condition of each seat or table within the establishment and also keep track of the presence of, for example, a seat that is being cleaned, and determines what task to do next.

A display that displays the status of each seat or table managed by the seat management system 204 (see FIG. 8) may be provided to the seat or table. The seat management system 204 holds information representing the correspondence between the ID of each seat or table, and the ID of the display provided to the seat or table. The seat management system 204 references the correspondence information, and transmits, to the corresponding display, information representing the status of each seat or table by using, for example, a wireless communication system such as a wireless LAN. The display displays a character string or pictogram representing the received status information. By looking at such information displayed on the display, a customer is able to learn whether a seat or table of interest is available (i.e., in "Vacant" status), or is unavailable for reasons such as the seat or table being currently used or reserved by another customer or the seat or table being currently cleaned.

Next, the following describes an example in which the sheet-shaped apparatus 100 is used to ensure the safety of a person sitting in a seat of a vehicle. In this example, information obtained from the sensor of the sheet-shaped apparatus 100 placed on the seat is combined with information indicating whether the seat belt on the seat is being worn. That is, by using information on the pressure distribution detected by the pressure distribution sensor 102 of the sheet-shaped apparatus 100, it is possible to determine whether the user is sitting in the seat with a good sitting posture. For example, by identifying where the peak of the pressure distribution is located with respect to the front-rear direction of the seating surface, it is possible to determine, for example, whether the user is sitting back in the seat with a correct posture or is conversely sitting on the front edge of the seat, or whether the user is sitting with an unbalanced posture to the left or right. The state of a user in a seat is safest when the user is sitting in the seat with a good posture and wearing a seat belt. Conversely speaking, if this condition is not satisfied, that is, if the user is not sitting with a correct posture or not wearing a seat belt, it is determined that a predetermined safety criterion is not satisfied for such a user, and the user or vehicle safety manager is notified to that effect.

In the present example, for each seat, the seat management system 204 receives, from the sheet-shaped apparatus 100 on the seat, pressure distribution data or the result of a determination made based on the pressure distribution data as to whether the sitting posture is good. Further, the seat management system 204 also receives, from a sensor or multiple sensors built in a seat belt provided to the seat, a signal indicative of whether the seat belt is being worn by the user sitting in the seat. In one example, a combination of the following sensors is used to sense whether the seat belt is being worn: a sensor that senses whether a tongue provided to the strap of the seat belt is fastened to the mating buckle; and a sensor that senses the tension applied to the strap. When the tongue of a seat belt on a vacant seat is being fastened to the buckle, the tension applied to the strap does not reach a threshold, whereas the tension applied to a seat belt that is being worn by a seated person becomes greater than or equal to the threshold. In the present example, a seat belt is determined to be correctly worn by the user in the seat if the tongue and the buckle are fastened to each other and the applied tension is greater than or equal to a threshold.

The seat management system 204 determines, based on a signal from each of the sheet-shaped apparatus 100 and a sensor provided to the seat belt, whether the sitting posture of the user sitting in the seat is good and whether the seat belt is being worn correctly. If it is determined that the sitting posture is poor or the seat belt is not being worn correctly, the seat management system 204 performs one or both of the following operations: displaying, on a display provided to the seat, a prompt prompting the user to correct his or her posture or to wear the seat belt; and displaying, on a display under the possession of a vehicle safety manager, a warning about the state of the user in the seat. Such display of a prompt or warning may inform the user which one of the user's posture and the way the user is wearing the seat belt is to be corrected.

In the above-mentioned case of a vehicle seat, the sheet-shaped apparatus 100 may be built in the seating portion or other portions of the seat, or may be tightly secured to the seat such as by being fit into a recess provided in the seating portion or other portions of the seat.

Examples of such a vehicle seat may be a seat in a passenger airplane, a seat in a passenger automobile, and a child car seat attached to a passenger automobile.

In another possible example, the sheet-shaped apparatus 100 is provided to each seat in a train, and a signal notifying whether a customer is seated in the seat is sent from the sheet-shaped apparatus 100 to the management apparatus 200 located within the train, so that information about whether a customer is seated in each seat is aggregated on the management apparatus 200 and the aggregated information is displayed on a terminal or other devices operated by the conductor or train operation manager. By looking at the displayed information, the conductor or other train staff personnel are able to learn which seat is being actually seated by a customer. The information thus obtained may be used for, for example, management of reserved seats.

Although the foregoing description is directed to an example in which the sheet-shaped apparatus 100 is in the form of a cushion placed on the seating surface of a seat, the sheet-shaped apparatus 100 may not necessarily be in the form of a cushion. For example, the sheet-shaped apparatus 100 may be a larger-sized, thin apparatus that can be also wrapped around the user's body like a lap robe when in use, for example.

Figure 9:
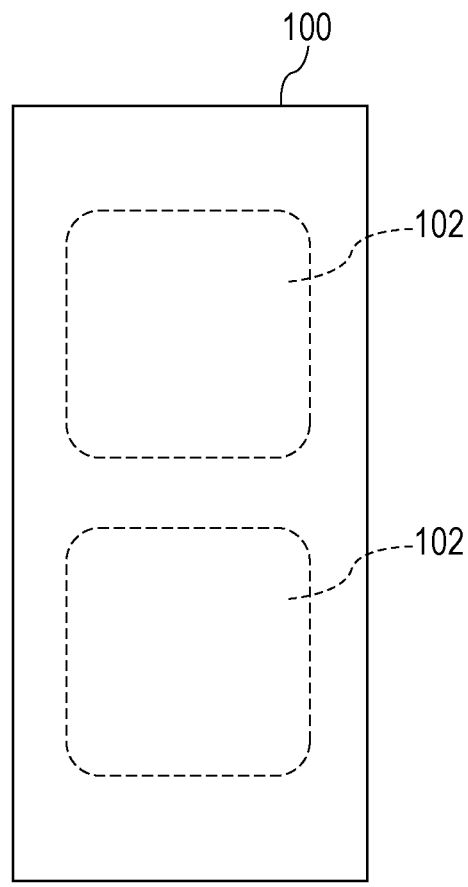
FIG. 9 schematically illustrates the top face configuration of a sheet-shaped apparatus used by being placed over the area from the seating surface to the backrest.
Figure 10:
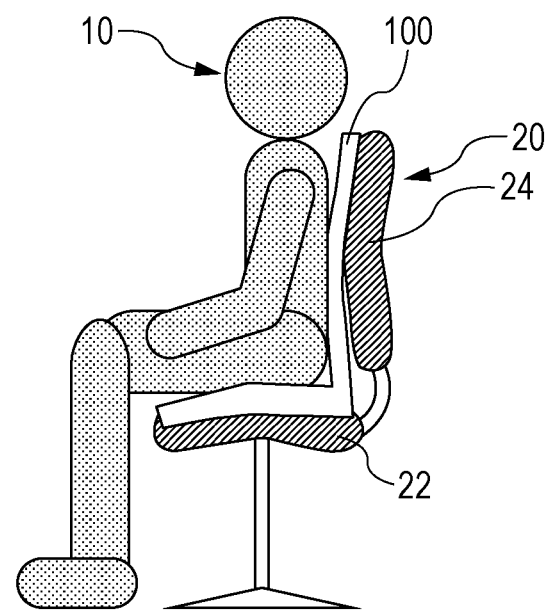
FIG. 10 schematically illustrates the sheet-shaped apparatus illustrated in FIG. 9 in use.

FIGS. 9 and 10 each illustrate such a larger-sized, thin sheet-shaped apparatus 100. The sheet-shaped apparatus 100 is, for example, a rectangular, relatively thin apparatus having a width approximately equal to the lateral width of a human person and a length approximately equal to the length from the neck or shoulders to the thighs of a human person. The term "relatively thin" as used herein means that the sheet-shaped apparatus 100 is of a thickness that allows the sheet-shaped apparatus 100 to be rolled or folded up for carrying. When in use, the sheet-shaped apparatus 100 is placed over the area of a chair 20 from a seating portion 22 to a backrest 24 as illustrated in FIG. 10. In FIG. 10, the sheet-shaped apparatus 100 is depicted thicker than in reality for easy recognition.

Although not illustrated, like the sheet-shaped apparatus 100 in the form of a cushion illustrated in FIGS. 1 and 2, the sheet-shaped apparatus 100 in the present example is also made up of the body portion 120 and a covering that covers the body portion 120. As described above, the body portion 120 is formed by the base 122 equipped with various sensors, such as the pressure distribution sensor 102 on each of the front and back sides of the base 122, and other electrical equipment, and the cover is made of, for example, a fabric or weave of natural fibers, such as wool, chemical fibers, or other fibers. The base 122 of the thin, sheet-shaped apparatus 100 in the present example is thinner than the base of the above-mentioned sheet-shaped apparatus 100 implemented as a cushion.

Since the sheet-shaped apparatus 100 in the present example is comparatively long, as illustrated in FIG. 10, the sheet-shaped apparatus 100 is placed such that approximately half of the sheet-shaped apparatus 100 is located on the seating surface of the seat, with the remaining approximately half of the sheet-shaped apparatus 100 resting against the backrest surface. Both the upper half and lower half of the sheet-shaped apparatus 100 may be provided with the pressure distribution sensor 102 so that whichever half of the sheet-shaped apparatus 100 may be placed on the seating surface.

When the user places the thin, sheet-shaped apparatus 100 over the area of the seat from the seating surface to the backrest and sits on the sheet-shaped apparatus 100, a pressure distribution is obtained from each of the pressure distribution sensor located on the seating surface and the pressure distribution sensor located on the backrest. If one of these sensors is sensing a load large enough to be determined as corresponding to the weight of a human person, it can be determined that the user is sitting on the sheet-shaped apparatus 100.

When the user uses the thin sheet-shaped apparatus 100 by placing the sheet-shaped apparatus 100 over the area of a vehicle seat from the backrest surface to the seating surface, the user is able to not only check if the user is sitting correctly over the seating surface based on information from the pressure distribution sensor 102 located on the seating surface, but also check if the user is leaning against the backrest surface with an appropriate force or posture based on information from the pressure distribution sensor 102 located on the backrest surface.

In one example, in addition to being placed on a seat when in use, the large-sized, thin sheet-shaped apparatus 100 illustrated in FIGS. 9 and 10 may be usable as a mat for fitness exercises. In the example in which the sheet-shaped apparatus 100 is also usable as a fitness mat, a sensor senses whether the sheet-shaped apparatus 100 is being bent, and in accordance with the result of this sensing, it is determined by, for example, the controller 110 or other devices (i.e., the controller 110 or the management apparatus 200) whether the sheet-shaped apparatus 100 is being placed over the area of the seat from the backrest to the seating portion, or is being laid flat on the floor for fitness exercises or other activities. If such bending is sensed, the sheet-shaped apparatus 100 may be determined as being placed on the seat, and if no such bending is sensed, the sheet-shaped apparatus 100 may be determined as being laid flat. As an example of a sensor to sense bending of the sheet-shaped apparatus 100, the pressure distribution sensor 102 in the shape of a sheet may be used. Although the example illustrated in FIG. 9 uses two pressure distribution sensors 102, one for the seating portion 22 and one for the backrest 24, for the present example in which the sheet-shaped apparatus 100 is used for fitness exercises, a single pressure distribution sensor 102 that covers a wide area extending from the seating portion 22 to the backrest 24 is used. In this case, when the sheet-shaped apparatus 100 is placed on the seat as illustrated in FIG. 10, an area bent with a relatively large radius of curvature is created near the longitudinally central portion of the sheet-shaped apparatus 100. The bent area near the central portion extends substantially linearly in the transverse direction of the sheet-shaped apparatus 100 across the entire lateral width of the sheet-shaped apparatus 100. For such a strongly bent area, the pressure distribution sensor 102 indicates a pressure value that is distinguishable from a pressure value corresponding to an area that is laid flat and on which the user is not sitting. The pressure applied to such a strongly bent area has a value far smaller than the value of the pressure applied by the user's body weight, and is thus distinguishable also from the pressure due to body weight. Accordingly, whether the sheet-shaped apparatus 100 is being placed on the seat or laid flat may be determined as follows. That is, the range of possible values taken by the pressure applied due to a bend occurring when the sheet-shaped apparatus 100 is placed on the seat is registered into the controller 110 or other devices in advance. When the sheet-shaped apparatus 100 is in use, if, at a location within the pressure distribution sensed by the pressure distribution sensor 102 that corresponds to the vicinity of the longitudinally central portion of the sheet-shaped apparatus 100, a pressure value that falls within the registered range is sensed across the entire lateral width of the sheet-shaped apparatus 100 with respect to the transverse direction, the sheet-shaped apparatus 100 is determined as being placed on the seat. Otherwise, the sheet-shaped apparatus 100 is determined as being laid flat.

When the user seats himself or herself on the sheet-shaped apparatus 100 placed on the seat, the user's body weight is distributed over a relatively wide area from the user's buttocks to the thighs. By contrast, when the sheet-shaped apparatus 100 is used as a fitness mat, the user assumes various postures, such as standing on the sheet-shaped apparatus 100 or supporting his or her body with the knees or elbows. When the sheet-shaped apparatus 100 is being used as a fitness mat as described above, the user's body weight is placed on areas far smaller than the buttocks, such as the sole, toe, knees, and elbows. In this regard, there are several types of body postures for fitness exercises (e.g., yoga or stretching), and which part of the body is to touch the mat is determined for each type of posture. Therefore, for each fitness exercise posture, it is possible to define a pressure distribution pattern that will appear in the plane of the sheet-shaped apparatus 100. Such different pressure distribution patterns for different fitness exercise postures are registered into the controller 110 or other devices in advance. If a pressure distribution matching a registered distribution pattern is sensed by the controller 110 or other devices while the sheet-shaped apparatus 100 is used while being laid flat, the user is determined to be assuming a posture corresponding to the pattern. In another example, the controller 110 or other devices may measure the duration of the posture, and record the posture assumed by the user and the duration of the posture. Such recorded information may be compiled for each unit period such as every day or every week, and presented to the user. An index of the effectiveness of a fitness exercise may be calculated from the recorded information (e.g., by calculating, for example, the amount of calorie consumed by the fitness exercise for each unit period as an index of exercise effectiveness, from the amount of calorie consumption per unit time for each different posture), and presented to the user.

The management apparatus 200 or other devices may manage the following pieces of information in association with each other: place information about the place where the above-mentioned fitness exercise is performed (e.g., identification information of a room, or identification information of a block within a room); and a description (e.g., the type or duration of each posture) of the fitness exercise. At this time, to recognize the place information, for example, a short-range wireless communication device built in the sheet-shaped apparatus 100 may receive identification information emitted by a beacon provided in a room or block, or conversely, a short-range wireless communication device (e.g., an NFC reader) provided in a room or block may receive the identification information of the sheet-shaped apparatus 100. The management apparatus 200 or other devices may analyze the correlation between the kind of a fitness exercise, and environmental information (e.g., temperature or humidity, or the name of the place) about the place where the fitness exercise is performed, and provide the results of the analysis to the user.

Although the sheet-shaped apparatus 100 includes the pressure distribution sensor 102 in each of the examples mentioned above, this is intended to be illustrative only. If it is only necessary to be able to sense whether the user is sitting on the sheet-shaped apparatus 100, the pressure distribution sensor 102 does not need to be used and, for example, a load sensor may be used instead of the pressure distribution sensor 102. Even for cases where it is necessary to determine a pressure distribution, instead of a sheet-shaped pressure distribution sensor, a set of multiple load sensors arranged in a given pattern within the plane of the sheet-shaped apparatus 100 may be used.

The foregoing description of the exemplary embodiment of the present invention has been provided for the purposes of illustration and description. It is not intended to be exhaustive or to limit the invention to the precise forms disclosed. Obviously, many modifications and variations will be apparent to practitioners skilled in the art. The embodiment was chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An information processing system comprising:
    a sheet-shaped apparatus placed in a specific location, the sheet-shaped apparatus including a sensor disposed in the sheet-shaped apparatus to sense information indicating whether a user is located over the specific location in which the sheet-shaped apparatus is placed; and
    a controller communicating with the sheet-shaped apparatus, the controller being configured to:
        acquire environmental information about the specific location;
        provide at least one of first information and second information based on the information sensed by the sensor and on the acquired environmental information, the first information representing a correspondence between a presence period and the environmental information for the presence period, the presence period being determined from the information sensed by the sensor and representing a time period for which the user has been present in the specific location, the second information representing a correspondence between a non-presence period and the environmental information for the non-presence period, the non-presence period being determined from the information sensed by the sensor and representing a time period for which the user has not been present in the location; and
        for a first location among a plurality of locations, which includes the specific location, provide the environmental information about the first location for the presence period, the first location being a higher-ranked location for which a length of the presence period within a predetermined period satisfies a predetermined condition among the plurality of locations.

2. The information processing system according to claim 1, wherein the controller is configured to, for a second location among the plurality of locations, provide the environmental information about the second location for the presence period, the second location being a lowered-ranked location for which a length of the presence period within a predetermined period satisfies a second predetermined condition among the plurality of locations.

3. The information processing system according to claim 1, wherein the controller is configured to, for a second location among the plurality of locations, provide the environmental information about the second location for the presence period, the second location being a lowered-ranked location for which a length of the presence period within a predetermined period satisfies a second predetermined condition among the plurality of locations.

4. An information processing system comprising:
    a sheet-shaped apparatus placed in a specific location, the sheet-shaped apparatus including a sensor disposed in the sheet-shaped apparatus to sense information indicating whether a user is located over the specific location in which the sheet-shaped apparatus is placed; and
    a controller communicating with the sheet-shaped apparatus, the controller being configured to:
        acquire environmental information about the specific location; and
        for each of a plurality of locations within a facility, and based on the information sensed by the sensor and on the acquired environmental information, cause a status of each location to transition and display a current status of the location based on a status transition instruction for the location and the information sensed by the sensor of the sheet-shaped apparatus corresponding to the location, the status transition instruction being an instruction given from a manager to cause a status of the location as the environmental information to transition.

5. The information processing system according to claim 4, wherein the controller is configured to notify a display of the current status of the location, the display being provided in association with the location.

6. The information processing system according to claim 1, wherein:
    the location includes a seat,
    the information processing system further includes a seat belt sensor that senses whether the user sitting in the seat is wearing a seat belt,
    the sensor disposed in the sheet-shaped apparatus senses information indicating whether a sitting posture of the user sitting in the seat is good, and
    the controller is configured to provide information indicating whether the sitting posture of the user in the seat satisfies a criterion, based on the information sensed by the sensor and indicating whether the sitting posture is good and based on the information sensed by the seat belt sensor as the environmental information.

7. The information processing system according to claim 1, wherein when the user is present on the sheet-shaped apparatus while doing an exercise, the provided information is changed in accordance with a kind of the exercise.

* * * * *